United States Patent [19]
Lewandowski

[11] Patent Number: 5,976,549
[45] Date of Patent: Nov. 2, 1999

[54] METHOD TO REDUCE BAD BREATH IN A PET BY ADMINISTERING RAW GARLIC

[76] Inventor: Joan Lewandowski, HC 63 Box 60, Costigan, Me. 04223

[21] Appl. No.: 09/118,421

[22] Filed: Jul. 17, 1998

[51] Int. Cl.[6] ............................ A61K 35/78; A61D 7/00; A23L 1/221; A23K 1/18
[52] U.S. Cl. ..................... 424/195.1; 424/442; 426/49; 426/54; 426/638; 426/805
[58] Field of Search ................. 424/195.1, 442; 426/49, 54, 638, 805; 119/707

[56] References Cited

U.S. PATENT DOCUMENTS

| | | | |
|---|---|---|---|
| 4,143,168 | 3/1979 | Bernotavicz | 426/266 |
| 4,763,604 | 8/1988 | Meekins | 119/1 |
| 4,771,733 | 9/1988 | Axelrod | 119/29.5 |
| 5,405,836 | 4/1995 | Richar et al. | 514/23 |
| 5,834,048 | 11/1998 | Erasmus et al. | 426/395 |

*Primary Examiner*—Kathleen K. Fonda
*Assistant Examiner*—Marjorie A. Moran
*Attorney, Agent, or Firm*—Thomas L. Bohan; Patricia M. Mathers

[57] ABSTRACT

An oral hygienic compound and method for use in domesticated animals such as cats and dogs. The primary component of the oral hygienic compound is pure, natural garlic. The method involves coating or otherwise adulterating the animal's food with the oral hygienic compound in order to maximize garlic exposure within the oral cavity of the animal. Thus, the oral hygienic compound should promote chewing by the animal so as to evenly distribute the garlic within the animal's mouth. Garlic, in an uncooked state, has been found to substantially eliminate a pet's bad breath, whether by substantially reducing odor-causing bacteria within the oral cavity, and/or by other more systemic means when it is administered according to the inventive method.

5 Claims, No Drawings

METHOD TO REDUCE BAD BREATH IN A PET BY ADMINISTERING RAW GARLIC

BACKGROUND OF THE INVENTION

1. Field of Invention

The present invention relates to the field of pet hygiene. More particularly, the present invention relates to controlling breath odor in pets. More particular yet, the present invention involves both a method and composition for controlling breath odor in pets such as dogs, where the active ingredient is uncooked garlic. Most particularly, the present invention involves the treatment and control of breath odor in pets by dispensing uncooked garlic in powder form to such pets.

2. Description of Prior Art

As all pet owners are aware, the smell of a pet's breath can be rank enough to repulse the pets' owners, as well as the owners' friends and relatives, thereby adversely affecting the emotional bond between dog and human. Just as there are remedies, such as mouthwashes, pastes, and gels, intended for human use in combating what the advertisers once dubbed "halitosis," so too are there "fresheners," i.e., cover-up liquids and solids, that can be administered to pets for what is referred to as "doggy breath." There are also chemical sprays and cleansers to be applied to the animal's oral cavity by the owner or by a veterinarian.

In particular, U.S. Pat. No. 4,525,341 issued Jun. 25, 1985, to Deihl discloses a method of administering vitamins to air-breathing animals (including humans) by an aerosol vehicle that, in addition to containing vitamins, also contains a breath freshener. The aerosol of Deihl is sprayed into the nose or mouth opening of the animal from where some of it is carried to the lungs by the animal's respiration. The "breath freshener" of Deihl not being specified, it can be any one of the products on the market bearing that name. As far as is known, none of these "fresheners" does more than temporarily mask the problem of bad breath in pets.

Richar et al. (U.S. Pat. No. 5,405,836 issued Apr. 11, 1995) disclose pet food containing water-soluble zinc compounds for controlling animal breath. This method avers that a primary source of offensive breath in animals results from the breakdown of food proteins by bacteria in the oral cavity. Thus, Richar et al. also teach that the zinc compounds can be incorporated into rawhide "chews" as a means of administering the bad-breath-controlling substance. Zinc sulfate is one such zinc compound that is widely known as a deodorant. However, it is not entirely a benign substance. Although the amounts of the compound that must be ingested in order to cause illness or death in a human or other big animals are large, they are proportionately smaller in small pets, and much more care must be taken in dispensing a safe dose. Thus, although it is possible to administer such compounds safely by using informed care, the potential for harm is present, therefore compromising the benefit of this approach to bad-breath control.

Except for Richar et al., all of the other prior-art breath improvements for animals have relied on sweet mint or chlorophyll-based scents, sprays, dietary supplements, etc. to simply mask the bad odors that are present. As indicated, these methods have at best resulted in a temporary cover-up of the undesirable odors.

To the extent that offensive odors arise from the oral cavity alone, it is known that scraping of plaque and tartar buildup from the animal's teeth is a further remedy, though one usually requiring the expertise and expense of a veterinarian, as animals frequently require sedation during such scraping. While tartar and plaque removal is effective and beneficial from a dental perspective, the offensive odors from the pet's mouth are neither entirely eliminated, nor even reduced for an appreciable amount of time. One reason for this is that scraping does not eliminate the odor-causing bacteria, but only a particular breeding place for such bacteria.

Another reason that scraping may not be sufficiently effective is that some of the strongest odors may not originate from the mouth at all. As with humans, these odors can emanate from the deep breath as a result of an adulterant present in the pet's system, especially the blood stream. Noxious gases, if present in the blood stream, can be given up by the blood during its oxygenation in the lungs, i.e., at the blood/lung interface. Several sources of such odors are known to be, for example, gas-producing vegetables, such as broccoli and Brussels sprouts, and cooked garlic.

Therefore, what is needed is a method for ameliorating offensive breath in domestic pets, especially in dogs, that can be easily administered by the pets' owners. What is also needed is that the method not be painful or expensive and that it give more than just temporary "cover-up" relief. What is further needed is a method that is benign to both the pet and the environment. Finally, what is need is such a method of breath amelioration that is acceptable to the pet.

SUMMARY OF THE INVENTION

The object of this invention is to provide a method of relieving bad breath in domestic pets that is easy for the pet owner to administer, that is effective in eliminating rather than simply masking the offensive odors, and that does not pose a danger of injury to the animal or to the environment.

The present invention arose from domestic canine feeding research conducted by the inventor that has led to the counterintuitive result that ingestion of raw garlic powder by dogs largely eliminates the bad breath—both local (in the mouth cavity) and systemic—that the subject animals otherwise regularly manifested.

Garlic-related products exist in many forms such as bulbs, whole cloves, and minced, chopped, crushed, liquefied, extracted, dried, and roasted preparations. In addition to its desirable attributes as a food seasoning, garlic in its many forms is thought to have some therapeutic benefits. Relatedly, garlic is used for many things including lowering blood pressure, reducing blood cholesterol, promoting cardiovascular activity, soothing the respiratory system, relieving gas and indigestion, reducing yeast infections, and providing a systemic insect repellent.

In the field of pet hygiene, the primary use of garlic heretofore has been as a flea repellant. Products relying on garlic for this purpose include "Garlic Pearls" offered by Hilton Canine Products and "Brewers Yeast With Garlic" offered by Four Paws (TM). Due to the systemic nature of the use of such products, however, each product is designed to maximize ingestion of the garlic within the digestive tract of the animal. This is done by encapsulating or otherwise compressing the garlic within a pill or capsule. Accordingly, the ability of such a small amount of so-ingested garlic or garlic-related compounds to affect the oral and nasal cavities of the animal is limited at best. Even if enough raw garlic is introduced systemically to produce some benefit in controlling the systemic contribution to bad breath as a side-effect, these products by their nature will not aid in the control of bad breath emanating locally from the oral and nasal cavities. As well, the use of this type of prior-art product is limited to systemic flea deterrence.

When considering garlic with respect to mouth odors, the commonly understood problem is that of "garlic-breath" present in human beings who have eaten some quantity of cooked garlic. A variety of mouthwashes, digestive aids, and oral hygiene products exists, presumably to counter the malodorous effects of garlic on human breath. Prior-art solutions purport to operate by either ridding one's mouth and body of the garlic scent after consumption or by somehow extracting the odor-causing compounds from the garlic prior to ingestion, the underlying point being that garlic is the root-cause of the oral odor problem. Thus, any assumption that garlic would promote pleasant breath in any animal—e.g., cats and dogs—runs counter to the apparently overwhelming common knowledge and experience, including that within the field of pet breath amelioration.

The observation by the inventor that something had caused the breath of her several dogs of various sizes and age to become unoffensive provided the stimulus to experiment with food and eventually led to the inventor's discovery that raw garlic greatly improved bad breath in dogs (and, by extension, other mammals kept as pets). Since the dogs were regularly fed "people food" in the form of table scraps and cooking samples, which they craved, it seemed reasonable to the inventor to conclude that something in the food that the dogs had managed to beg from the cook was effecting a reduction in the dogs' bad breath. In order to identify which of the various daily cooking ingredients had caused the change in the dogs' breath, the inventor conducted a series of tests on her six dogs over testing periods of two days each. The medium upon which varied ingredients were placed was ground beef. The ingredients tested included:

1) onions browned in olive oil and mixed with fried ground beef;
2) garlic browned in olive oil and mixed with fried ground beef;
3) garlic and onions browned in olive oil and mixed with fried ground beef;
4) garlic and onions browned in olive oil and cooked with canned tomatoes (tomatoes being known for their ability to eliminate certain odors, such as skunk) and mixed with fried ground beef;
5) ground beef patties coated with onion powder and then broiled;
6) ground beef patties coated with garlic powder and then broiled;
7) ground beef patties coated with ground sage and then broiled.

Each of items #1 through #7, when cooled and fed to the dogs, produced no change in the dogs' bad breath. After considering these results, testing procedures were then re-evaluated, leading to the belief that certain spices introduced after cooking might have caused the elimination of the dogs' offensive breath. Accordingly, the following combinations were fed to the dogs over a testing period of two days for each recipe:

8) broiled ground beef patties sprinkled after cooking with onion powder;
9) broiled ground beef patties sprinkled after cooking with ground sage;
10) broiled ground beef patties sprinkled after cooking with parmesan cheese;
11) broiled ground beef patty sprinkled after cooking with garlic powder.

None of items #8 through #10, when fed to the dogs, produced any change in the dogs' bad breath. However, feeding the dogs ground beef coated with garlic powder (Item #11) resulted in the elimination of all offensive dog breath odor. This phenomenon was observed to last well into the next day's feeding, as much as 24 hours later. Additional experiments have shown that the effect of garlic powder on a dog's breath lasts at least 48 hours and on occasion up to 72 hours. In order to verify the beneficial and counterintuitive results of using uncooked garlic to substantially eliminate bad breath in dogs, garlic powder was thereafter used to coat all the dogs' meals. This eliminated bad breath from all of the dogs tested. Further, upon ceasing the use of garlic powder on each dogs' meals, the bad breath returned after a few days.

To confirm these results, garlic powder was administered to two additional dogs and to two litters, each litter consisting of 6 puppies. In all 14 animals, bad breath—including "puppy breath"—was eliminated. Thus, garlic in its uncooked state was verified as means for eliminating bad breath in dogs.

It is not clear why the inventor's method works to eliminate bad breath. It is known that crushed garlic contains an enzyme, allinase, which is known to have some bactericidal effects. It is reasonable to suppose that some of the odors present in offensive breath are caused by bacteria present in the oral and nasal cavities and that the application of allinase through the medium of garlic kills that bacteria and hence the odor arising from them. Inventor's experiments have shown that delivery of raw garlic to the animal in a manner that will maximize the degree of direct contact of the garlic with the teeth and tissue in the mouth cavity of the animal, e.g., by sprinkling a coating of garlic powder on the animal's food, is effective in eliminating offensive mouth odor. Delivering raw garlic to an animal in a form that will allow the garlic to enter the animal's digestive tract without contacting to any large extent the teeth and tissue in the mouth cavity of the animal, such as by delivering the garlic in a capsule, may provide some benefit in that the garlic may be effective systemically, i.e. killing odors that arise in the system of the animal, but it may not have the desired beneficial effect on offensive breath that is caused by the presence of odor-causing bacteria in the mouth. It is also significant that cooking (i.e., heating) the garlic destroys the desired effect on the animals' breath.

It is an object of the present invention to deliver raw garlic to a pet in a way that is both easy for the pet owner and acceptable to and safe for the animal. Thus, dispensing raw garlic powder from a special shaker onto the animal's food, for example, is one convenient method of achieving the desired effect. Alternatively, one can also prepare rawhide products, dog biscuits, cat treats, and the like for the delivery of the raw garlic cure to pets. Similar ingenuity can be used to apply raw garlic, as dry powder or wet coating, for example, to such items as dog and cat toys, such as by coating catnip impregnated objects with the raw garlic.

It is to be understood that other objects and advantages of the present invention will be made apparent by the following description of the drawings according to the present invention. While a preferred embodiment is disclosed, this is not intended to be limiting. Rather, the general principles set forth herein are considered to be merely illustrative of the scope of the present invention and it is to be further understood that numerous changes may be made without straying from the scope of the present invention.

THE PREFERRED EMBODIMENT

Uncooked natural garlic added to a dog's meal or snack has been discovered by the inventor to reduce unpleasant odors—colloquially referred to as "doggie breath"—within the dog's oral cavity as well as in the dog's system. The active ingredient in the raw garlic may be the enzyme, allinase. Therefore, it should be noted that while allinase in its purified form, either extracted from garlic or synthetically produced, may indeed work to rid one's pet of bad breath in accordance with the present invention, the inexpensive and more natural form of powdered garlic is preferred.

Thus, in the Preferred Embodiment of the invention, a coating of garlic powder prepared from uncooked garlic is applied as a coating to a dog's food and snacks. In order to assure the delivery of the raw garlic, the coating should preferably be applied to the dog's food during processing. Thus, dog owner's would purchase dog food and snacks having the coating already in place.

It should be understood that the Preferred Embodiment mentioned here is merely illustrative of the present invention. Numerous variations in design and use of the present invention may be contemplated in view of the following claims without straying from the intended scope and field of the invention herein disclosed.

I claim:

1. A method for reducing offensive breath of a mammalian pet, said method comprising:

a) applying raw garlic to a delivery system item that is appealing to said pet, b) presenting said garlic and said delivery system to said pet, and c) allowing said pet to ingest said raw garlic, thereby causing said garlic to come into contact with tissue within an oral cavity of said pet.

2. The method as claimed in claim 1 wherein said garlic is in the form of garlic powder.

3. The method as claimed in claim 1 wherein said garlic is in the form of garlic powder in a liquid suspension.

4. The method as claimed in claim 1 wherein said delivery system is in the form of food consumed by said pet.

5. The method as claimed in claim 1 wherein said delivery system is in the form of an item chewed by said pet.

* * * * *